US008348895B1

(12) United States Patent
Vitello

(10) Patent No.: US 8,348,895 B1
(45) Date of Patent: Jan. 8, 2013

(54) TAMPER EVIDENT CAP ASSEMBLY

(75) Inventor: Jonathan Vitello, Ft Lauderdale, FL (US)

(73) Assignee: Medical Device Engineering, LLC., Pompano Beach, FL (US)

( * ) Notice: Subject to any disclaimer, the term of this patent is extended or adjusted under 35 U.S.C. 154(b) by 271 days.

(21) Appl. No.: 12/800,991

(22) Filed: May 27, 2010

(51) Int. Cl.
*A61M 5/00* (2006.01)
*A61M 5/24* (2006.01)
*A61M 5/14* (2006.01)
*B65D 41/32* (2006.01)
*B65D 39/00* (2006.01)

(52) U.S. Cl. ........ 604/111; 220/266; 215/253; 604/200; 604/256

(58) Field of Classification Search .................. 215/250, 215/251, 252, 253; 220/265, 266; 604/111, 604/200, 256
See application file for complete search history.

(56) References Cited

U.S. PATENT DOCUMENTS

| | | | |
|---|---|---|---|
| 3,245,567 A | 4/1966 | Knight | |
| 3,747,751 A | 7/1973 | Miller et al. | |
| 4,216,872 A | 8/1980 | Bean | |
| 4,313,539 A | 2/1982 | Raines | |
| 4,420,085 A | 12/1983 | Wilson et al. | |
| 4,571,242 A | 2/1986 | Klein et al. | |
| 4,667,837 A | 5/1987 | Vitello et al. | |
| 4,726,483 A * | 2/1988 | Drozd | 215/252 |
| 4,832,695 A | 5/1989 | Rosenberg et al. | |
| 4,844,906 A | 7/1989 | Hermelin et al. | |
| 5,009,323 A * | 4/1991 | Montgomery et al. | 215/252 |
| 5,135,496 A | 8/1992 | Vetter et al. | |
| 5,165,560 A | 11/1992 | Ennis, III et al. | |
| 5,328,474 A | 7/1994 | Raines | |
| 5,458,580 A * | 10/1995 | Hajishoreh | 604/240 |
| 5,558,648 A | 9/1996 | Shields | |
| 5,624,402 A * | 4/1997 | Imbert | 604/111 |
| 5,807,343 A | 9/1998 | Tucker et al. | |
| 5,883,806 A | 3/1999 | Meador et al. | |
| 6,000,548 A | 12/1999 | Tsals | |
| 6,126,640 A | 10/2000 | Tucker et al. | |
| 6,190,364 B1 * | 2/2001 | Imbert | 604/256 |
| 6,193,688 B1 | 2/2001 | Balestracci et al. | |
| 6,196,998 B1 * | 3/2001 | Jansen et al. | 604/111 |
| 6,280,418 B1 * | 8/2001 | Reinhard et al. | 604/187 |
| 6,394,983 B1 * | 5/2002 | Mayoral et al. | 604/192 |
| 6,485,460 B2 | 11/2002 | Eakins et al. | |
| 6,565,529 B1 | 5/2003 | Kimber et al. | |
| 6,581,792 B1 * | 6/2003 | Limanjaya | 215/252 |
| 6,585,691 B1 * | 7/2003 | Vitello | 604/111 |
| 6,726,652 B2 | 4/2004 | Eakins et al. | |
| 6,726,672 B1 * | 4/2004 | Hanly et al. | 604/414 |
| 6,921,383 B2 | 7/2005 | Vitello | |

(Continued)

*Primary Examiner* — Kevin C Sirmons
*Assistant Examiner* — William Carpenter
(74) *Attorney, Agent, or Firm* — Malloy & Malloy, P.L.

(57) ABSTRACT

The tamper evident cap assembly is structured for protective connection to a syringe of the type having a nozzle and a discharge port, wherein the cap assembly includes a body configured to receive and access to the nozzle. A flow restricting member is connected to the body to at least initially define a one piece construction. The flow restricting member is disposed in flow restricting relation to the discharge port of the nozzle. An attachment assembly interconnects the body and the flow restricting member and is structured, such as by being frangible to facilitate detachment of the body from the flow restricting member upon the body being removed from the syringe. A connecting assembly is structured for a snap-fit connection to the nozzle and retains the flow restricting member thereon upon removal of the body from the syringe.

17 Claims, 3 Drawing Sheets

U.S. PATENT DOCUMENTS

| | | |
|---|---|---|
| 6,942,643 B2 | 9/2005 | Eakins et al. |
| 7,141,286 B1 | 11/2006 | Kessler et al. |
| 7,588,563 B2 | 9/2009 | Guala |
| 7,641,636 B2 * | 1/2010 | Moesli et al. ............... 604/198 |
| 7,735,664 B1 * | 6/2010 | Peters et al. ................ 215/44 |
| 7,762,988 B1 | 7/2010 | Vitello |
| 2002/0133119 A1 | 9/2002 | Eakins et al. |
| 2004/0064095 A1 | 4/2004 | Vitello |
| 2004/0116858 A1 * | 6/2004 | Heinz et al. ............... 604/111 |
| 2004/0225258 A1 * | 11/2004 | Balestracci ............... 604/111 |

* cited by examiner

TAMPER EVIDENT CAP ASSEMBLY

BACKGROUND OF THE INVENTION

1. Field of the Invention

This invention is directed to a tamper evident cap assembly that is connectable to a fluid loaded syringe in protective, sealing relation to a nozzle and discharge port of the syringe. A body includes a flow restricting member interconnected to define a one piece construction of the cap assembly. The flow restricting member is structured to facilitate a snap-fit connection of the cap assembly on the syringe, thereby sealing the discharge port thereof. Tampering is indicated by a separation of the flow restricting member and the body and a detachment of the body from the syringe when a predetermined force, sufficient to remove the body from the syringe, is exerted on the body.

2. Description of the Related Art

In hospitals or other medical care facilities, it is common for authorized medical personnel to order that a patient be given a drug or medication by injection. As a result, a number of syringes may be pre-loaded or filled by a pharmacist or other authorized personnel within the hospital or other facility, at a location which may be generally referred to as a syringe filling station. However, such a syringe filling station is typically located in a remote part of the facility, relative to the patient care area where the injection is to be administered. Indeed, at large medical facilities, a syringe filling station may resemble a factory on the hospital grounds from which drug loaded syringes are delivered to multiple nurse's stations in multiple other hospital buildings. Because of the remote location of many nurse's stations, relative to a syringe filling station, a loaded syringe is very often given to another person for delivery to a nurse's station for subsequent dosing of the patient by a duly qualified nurse or other medically trained person.

Also, especially in the case of a very expensive drug or an addictive type of drug that has been prescribed, such as but not limited to morphine, there is a danger that the pre-loaded syringe will be tampered with at some point, by a person seeking to improperly gain unauthorized access to the contents thereof. This possibility can present real danger if such person were to gain access to the prescribed medicine and then, inappropriately and without concern, substitute some other, unauthorized material in the syringe which looks like the actual prescribed medicine and dosage. By way of an example only, if saline solution were substituted for a dose of morphine, this could have extremely serious consequences. Thus, there is a problem of knowing if a sealed, preloaded syringe has, or has not, been exposed to contamination or might otherwise have been compromised by it being tampered with. This and related types of problems have been described in the inventor's own previously granted U.S. Pat. No. 4,667,837 and in other patents, such as U.S. Pat. No. 5,328,474.

However, certain problems remain in the relevant field of art, despite the introduction of products according to those two patents. These include problems of manufacturing such products in a manner which is relatively easy and inexpensive, as well as some problems involved with the assembly and placement onto a drug loaded syringe, such as at a drug filling station. Other problems exist relative to maintaining the sterility during storage at the manufacturing facility of the end caps, and during transport of them to another medical facility, and during storage of them at a medical facility. In summary, the present invention seeks to, address such problems and others associated with the handling of tamper evident end caps during the manufacturing of them, assembly of them and/or use at different stations and/or by different persons.

Accordingly, there is a need in this area for an improved, tamper evident, end cap assembly which is capable of being used with standard or conventional pre-loaded syringes in a manner which overcomes problems and or disadvantages of the type set forth above. If any such improved end cap assembly were developed, it would preferably have certain structural and operative features such as, but not limited to, being at least initially of a one piece construction in order to facilitate appropriate connection to a preloaded syringe. In addition, if any such improved end cap assembly were developed, it would preferably also be structured to provide a clear and unmistakable indication of tampering or of previous access to the contents of the preloaded syringe. Finally, if any such improved, tamper evident end cap assembly were developed, it would ideally also be structurally and operatively reliable, while still remaining relative easy and cost effective to make and assemble, in order to facilitate widespread use and acceptance through out the medical profession.

SUMMARY OF THE INVENTION

The present invention is intended to present a solution to these and other needs which remain in the relevant field of art, and as such, is directed to a tamper evident cap assembly structured for being protectively connected to a syringe of the type including a nozzle and a discharge port, with a representative type of conventional syringe from the prior art being shown in FIG. 1 of the appended drawings. For purposes of clarity, in describing the structural and operative features of the present invention, reference will be made to a conventional or standard syringe 11 of the type represented in FIG. 1. As such, the syringe 11 typically includes a barrel 1 and a nozzle 2. The barrel 1 comprises an elongate interior chamber disposed in fluid communication with an axial passageway or channel 3 on the interior of the nozzle tube or like nozzle portion 2', which may comprise a portion of a luer type fitting. The channel 3 is to be considered a portion of the nozzle 2 and terminates distally at an opening or discharge port 4. A piston 5 is slidable within the barrel and includes a head 6 provided with a circumferential gasket means 7. When assembled, the end face 9 of the head 6 of the piston confronts the interior end of the channel 3 and closes the discharge port 4. The piston also includes a push rod or plunger 8 is connected to the head 6 and is dimensioned to pass into the barrel 1. In use, the standard type syringe 11, after being loaded with its intended contents, is sealed by closing the discharge port 4 with a syringe cap or like closure. Accordingly, the nozzle 2 preferably includes an inner connecting surface 3" or other appropriate connecting structure, such as a ribbed or threaded surface. Therefore for the purpose of fully and accurately describing the tamper evident cap assembly of the present invention, the interior connecting surface or portion 3" and the tube or like nozzle portion 2' are to be considered a part of the nozzle 2.

The tamper evident cap assembly of the present invention comprises a body including a nozzle engaging portion defined by a flow restricting member. When the body is connected to the syringe, the flow restricting member is disposed to restrict fluid flow from the discharge port of the nozzle and is cooperatively structured with a remainder of the body to provide a clear indication of an attempted or accomplished access to the contents of the preloaded syringe. In addition, the body and the flow restricting member are further cooperatively structured to at least initially define a one piece construction of the body and flow restricting member.

An attachment assembly is disposed in interconnecting relation between the body and the flow restricting member. Moreover, the attachment assembly may include at least one, but possibly a plurality of attachment members disposed in the aforementioned interconnecting relation and being structured to facilitate disconnection or detachment of the body and the flow restricting member, when a sufficient force is exerted on the body to cause its removal from the syringe. Therefore as generally set forth above, the provision of the frangible or other detachably structured attachment assembly in interconnecting relation between the body and the flow restricting member serves to at least initially define a one piece construction of the tamper evident cap assembly. Such a one piece construction remains in tact prior to the removal of the body from the syringe. However, separation of the body from the flow restricting member and from the syringe nozzle is indicative of attempted access to the contents of the syringe.

In addition, the tamper evident cap assembly also comprises a connecting assembly mounted on the flow restricting member and disposed and structured to retain the flow restricting member on the nozzle of the syringe. As such, the connecting assembly serves to retain the flow restricting member in covering or otherwise flow restricting relation to the discharge port of the nozzle of the syringe, thereby eliminating or restricting the flow of the preloaded drug or fluid within the syringe from exiting through the discharge port. Additional features of the connecting assembly include a cooperative structuring thereof with the nozzle portion of the syringe so as to facilitate a quick, efficient "snap-fit" connection between the flow restricting member and the nozzle. As such, the attachment of the tamper evident cap assembly as well as the removal thereof from a conventional syringe is significantly facilitated by eliminating any need to rotate portions of the tamper evident cap relative to the nozzle during procedures such as, but not limited to, filling and/or refilling procedures performed by a pharmacist or other authorized personnel. It is generally recognized that individuals involved with the prefilling operation of the syringe, which may occur over numerous times over a given period, encounter stressful, operating conditions when significant handling or manipulation of the syringe, is required. Such stressful conditions at least sometimes result in carpel tunnel syndrome or other stress related disorders to the authorized personnel.

Accordingly, the connecting assembly serving to interconnect the flow restricting member and the remaining portions of the body to the syringe is structured to accomplish the aforementioned snap-fit connection to a portion of the nozzle of the syringe by substantially linearly directing the cap assembly towards and onto the nozzle portion when the flow restricting member is substantially coaxially disposed relative to nozzle. More specifically, the preferred snap-fit connection is facilitated due to the provision of a plurality of legs flexibly connected to the flow restricting member. Each of the flexible legs includes a free, distal end having an outwardly projecting lip or like structure formed thereon. Again with reference to the prior art representation of FIG. 1, a linear positioning of the cap assembly of the present invention towards the nozzle 2, while the flow restricting member is substantially coaxially aligned with the interior tube or like nozzle portion 2' will cause the plurality of flexible legs to pass into interior, connecting portions of the nozzle 2 and engage the interior connecting surface 3", which, may be threaded or other wise appropriately structured.

As a result of such a snap fit connection, the connecting assembly will serve to retain the body of the cap assembly and in particular flow restricting member in enclosing relation with a portion of the nozzle and in flow restricting relation to the discharge port thereof. Accordingly, once the tamper evident cap assembly is operatively positioned on the syringe, a predetermined force being exerted on the body, in attempt to remove it from the syringe will be at least partially transferred to the flow restricting member, resulting in a breakage or detachment of the attachment member or members. This in turn will result in a removal or disconnection of the body of the tamper evident cap assembly from the nozzle of the syringe due to the frangible nature or other breakable structure of the attachment assembly. However, due to the retaining engagement of the connecting assembly with the interior, connecting portion of the nozzle, the flow restricting member will remain on the nozzle in flow restricting relation to the discharge port. Such will be a clear indication that attempts have been made to use the syringe and/or access the contents on the interior thereof.

Upon removal of the body, authorized use of the syringe and/or access to the contents thereof can be accomplished by exerting an additional pulling force on the flow restricting member remaining on the nozzle of the syringe. As such, the lips of the flexible legs of the connecting assembly will be forced from their retaining, biased engagement with the connecting portions of the nozzle of the syringe.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
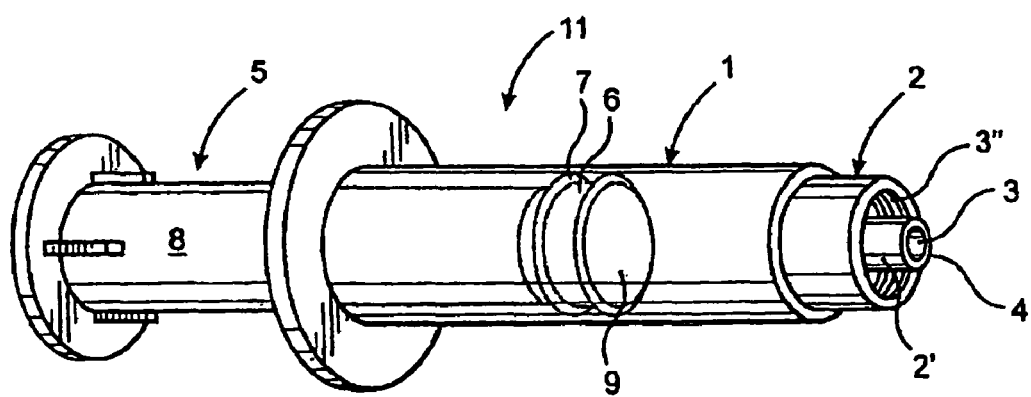
FIG. 1 is a perspective view of a prior art representation of a conventional or standard syringe structure of the type with which the tamper evident cap assembly of the present invention may be used.
Figure 2:
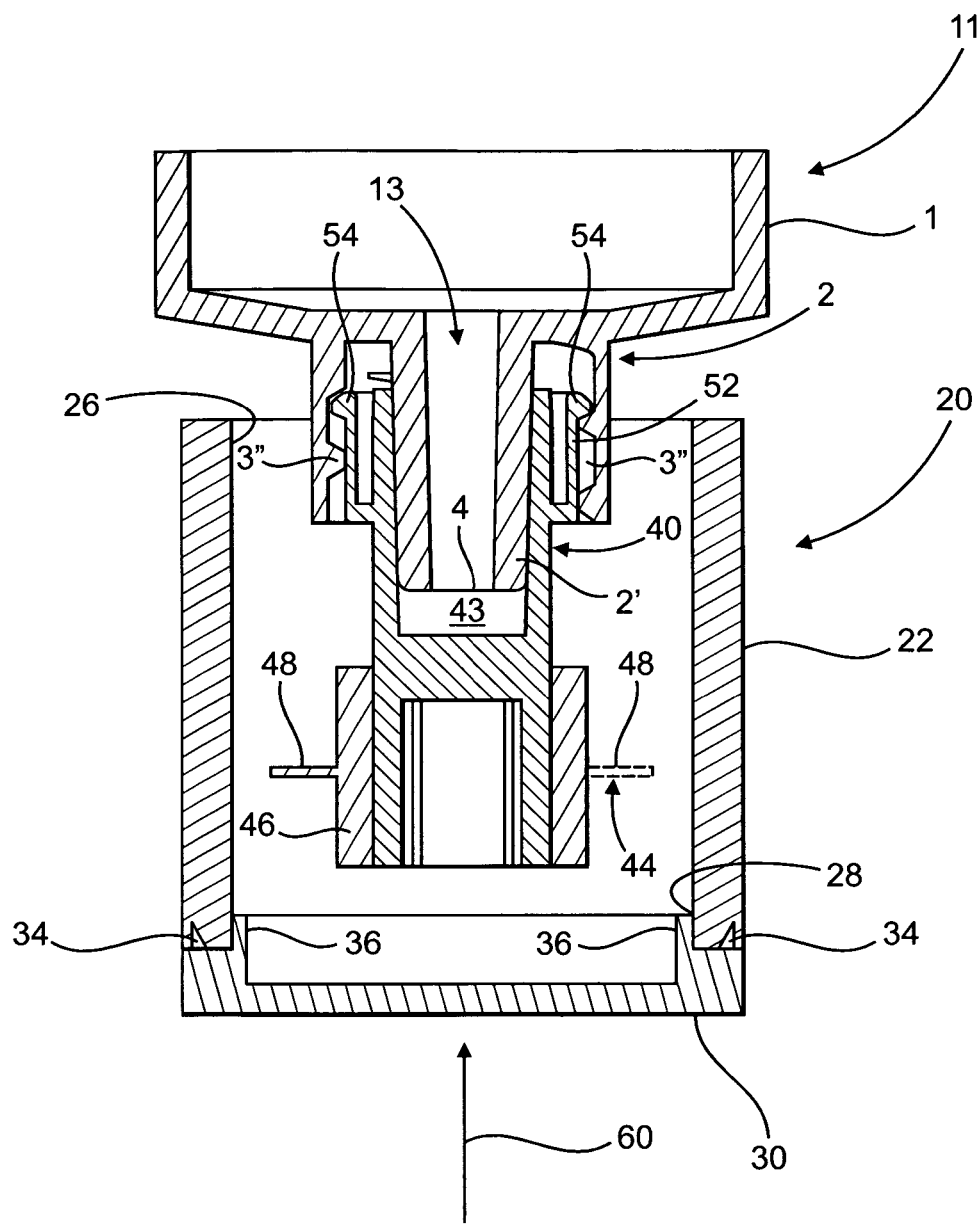
FIG. 2 is a sectional view in partial cutaway of the tamper evident cap assembly of the present invention operatively connected to the nozzle of a prior art or standard syringe, which may be of the type represented in FIG. 1.
Figure 3:
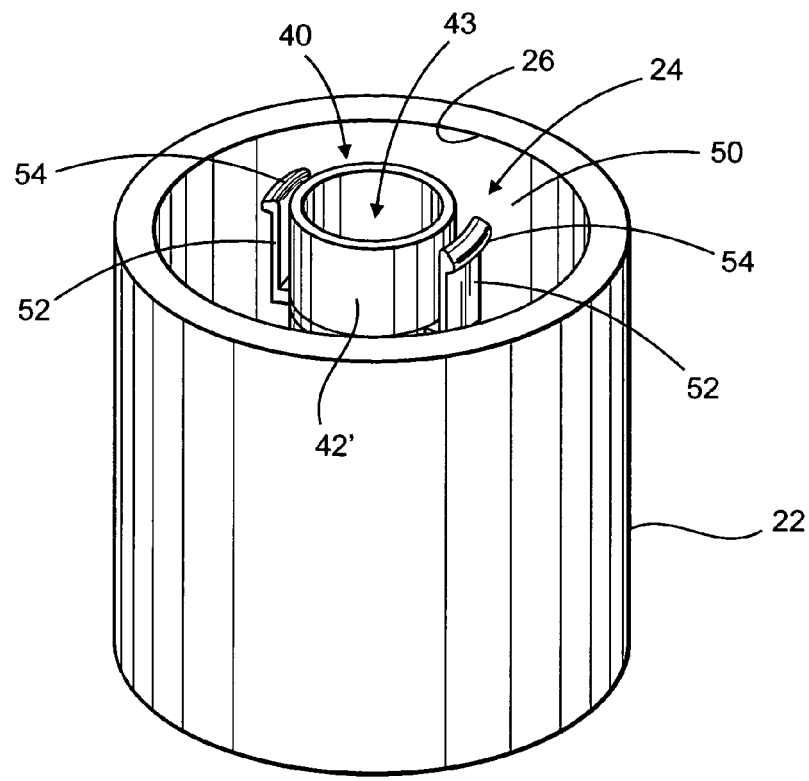
FIG. 3 is a top perspective view of the body portion and a flow restricting member, connected as a one piece construction on an interior of the body, wherein the body is in a non-connected orientation relative to a syringe.
Figure 4:
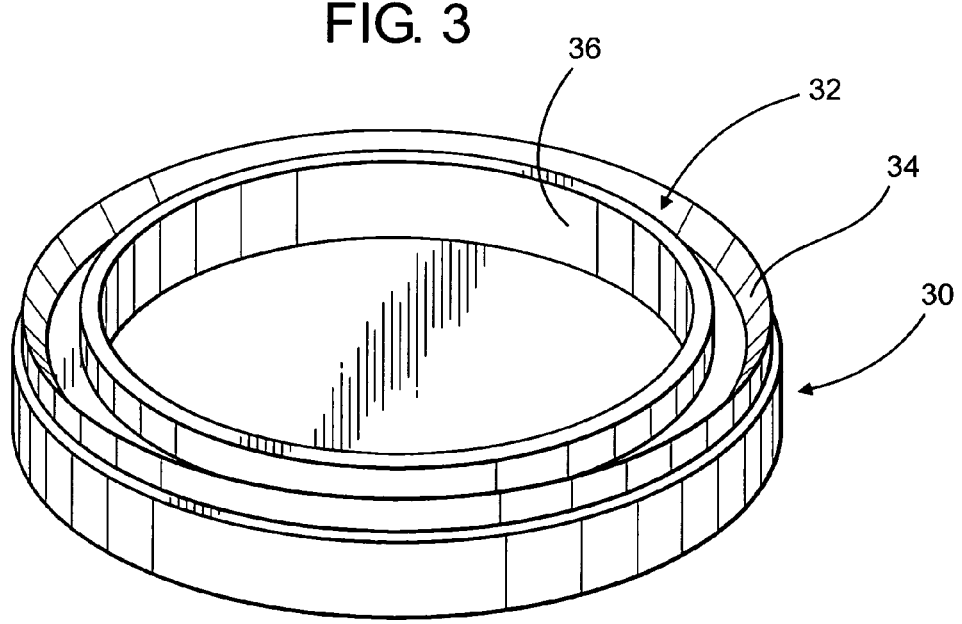
FIG. 4 is a perspective view of a base or end cap of the body of the embodiment of FIGS. 2 and 3.

With primary reference to FIGS. 2-4, the present invention is directed to a tamper evident cap assembly and is generally indicated by reference numeral 20. As set forth above, the cap assembly 20 is intended to be used on or in combination with a conventional or standard type syringe 11, represented as prior art in the above noted embodiment of FIG. 1. It is emphasized that the prior art syringe of FIG. 1 is representative only of a plurality of different conventional or standard syringes which may differ from one another in various structural features. However, as will be apparent from the detailed description hereinafter provided, the mounting or connection of the cap assembly 20 to the nozzle 2 of the syringe will prevent fluid discharge from the interior channel 3 and/or discharge port 4. As a result, the flow or discharge of fluid from the interior of the syringe 11 will be prevented unless the cap assembly 20 is removed from the nozzle 2.

In order to clearly describe the structural and operative features of the tamper evident cap assembly 20, FIG. 2 represents its assembled and connected orientation to the syringe 11. Moreover, when operatively connected in the intended manner of FIG. 2, the components the cap assembly 20 interact with the nozzle assembly 2 not only to restrict access to the contents of the syringe 11, but also to provide a clear indication of such access, whether authorized or not.

Accordingly the cap assembly 20 includes a body 22 having an at least partially hollow interior portion 24 dimensioned to receive the nozzle 2 therein. When the nozzle 2 is disposed within the interior 24, it is substantially surrounded by the cylindrical body 22, when the cap assembly 20 is operatively connected to the syringe 11. As such, the body 22 comprises a substantially cylindrical shell having an open end 26 dimensioned to allow passage therethrough of the nozzle 2 including the nozzle portion or tube 2'. As represented, the nozzle portion 2' includes an interior channel 3 disposed in communicating relation with the interior of the barrel 1 of the syringe 11. The elongated channel 3 terminates in an open discharge port 4 through which fluid, preloaded into the barrel 1 of the syringe 11, may be discharged. The opposite end 28 of the body 22 is closed in order to prevent access to the nozzle 2 or interior 24 of the body 22 when connected to the nozzle 2 in the intended manner.

More specifically, the opposite or distal end 28 of the body 22 is closed through the provision of an end cap member 30. The end cap member 30 may be fixedly connected in closing or covering relation to the distal end 28 as indicated in FIG. 2. The end cap 30 may be integrally secured to the body 22. However, a preferred embodiment of the tamper evident cap assembly 20 comprises the provision of a continuous, peripheral portion 32 structured to include an outer protruding ring or like member 34. When secured to the body 22, the protruding ring 34 is disposed and structured to fit within a cooperatively dimensioned annular recess formed in the end 28, as also represented in FIG. 2. A secure connection of the end cap 30 on the end 28 of the body 22 may be further facilitated by an inner, annular flange 36, which will be at least partially disposed on the interior of the distal end 28, as also represented in FIG. 2.

Another structural and operative feature of the present invention comprises the provision of a nozzle engaging portion generally indicated as 40, which is defined by a flow restricting member 42. The nozzle engaging portion 40 and/or flow restricting member 42 is connected directly to the interior 24 of the body 22 by an attachment assembly generally indicated as 44. As such, the body 22 and the flow restricting member 42 define, at least initially, a one piece construction which is connectable to the nozzle 2 of the standard syringe 11 as a single, integrated unit. The attachment assembly 44 may include a base 46 which is fixedly connected to a correspondingly disposed portion of the flow restricting member 42. The connection of the base 46 and the flow restricting member 42 may be by an integral attachment, a secure frictional engagement and/or another appropriate fixed securement. Regardless of the specific type of fixed connection between the base 46 and the corresponding portion of the flow restricting member 42, it is again emphasized that the flow restricting member 42 and the body 22 define a one piece construction of the tamper evident cap assembly 20.

Additional structural features of the attachment assembly 44 include at least one or alternatively, a plurality of attachment members 48 disposed in interconnecting relation between the exterior of the flow restricting member 42 and an interior surface or other interior portion of the body 22. Moreover, one or more of the attachment members 48 are formed of a frangible material or include other breakable or detachable structures which facilitates a detachment of the flow restricting member 42 from the interior of the body 22 when an adequate or predetermine force is applied to the attachment assembly 44 and or body 22. Accordingly, when a predetermined force is applied to the body 22 of sufficient magnitude to remove it from the syringe 11, at least a portion of such force will be transferred to the frangible or breakable material attachment member(s) 48. Therefore, attempts to remove the body 22 from the syringe 11, by applying such a predetermined force, will cause a disconnection of the flow restricting member 42 from the interior surface or other interior portion of the body 22, to which it is interconnected.

As represented, the body 22 is primarily, if not exclusively, secured to the nozzle 2 of the syringe 11 by virtue of the interconnection of the attachment assembly 44 between the flow restricting member 42 and the body 22. As a result, a fracturing or breakage of the one or more attachment members 48, due to a sufficient predetermined force being applied thereto, will cause detachment of the body 22 from the nozzle 2 and most probably a removal of the body 22 from its surrounding, at least partially enclosing relation to the nozzle 2. Moreover, the degree of force required for breakage or detachment of the one or more attachment members 48 is determined and effectively regulated by the material from which the attachment members 48 are formed and/or the number of attachment members utilized. Accordingly, the force required to fracture or break the one or more attachment members 48 should be such as to allow at least a sufficient force to be applied to the body 22 to accomplish its connection, in the intended operative orientation to the nozzle 2, as represented in FIG. 2.

With primary reference to FIGS. 2 and 3, yet additional features of the present invention include a connecting assembly generally indicated as 50 comprising a plurality of at least two legs 52 each formed of a flexible material and connected to the proximal end 42' of the flow restricting member 42. Each of the legs 52 are disposed on opposite sides of the end 42' of the flow restricting member 42 in preferably opposing relation to one another as indicated. Moreover, each of the legs 52 include an outwardly projecting or extending lip 54 connected to the free end thereof. Due to the flexibility of the legs 52 and by virtue of the ends to which the lips 54 are attached being "free" or unattached ends, each of the legs 52 will demonstrate a degree of flexibility when disposed into the operative, connected orientation represented in FIG. 2.

The flexible nature of the legs 52 serve to at least partially facilitate a "snap fit" connection between the nozzle 2 and the legs 52 as they pass into the interior of the nozzle 2 and engage connecting portions 3" thereof. Such a snap fit connection is accomplished by linearly directing the cap assembly 20 towards the nozzle, such as by applying a substantially linear force to the body in a direction towards the nozzle 2, as schematically indicated by arrow 60. Concurrently, the interior 43 of the flow restricting member 42 is disposed in substantially coaxial alignment with the tube or nozzle portion 2' of the nozzle 2. The provision of the internal connecting portion or surface 3" having an at least partially threaded, ribbed or other appropriate structure, will serve to at least partially retain the lips 54 into retaining engagement with the connecting portion 3". This connection between the flow restricting member 42 and the nozzle 2 will serve to maintain the flow restricting member 42 on the nozzle 2, even when a predetermined force is applied to the exterior of the body 22 in an attempt to remove it from the syringe 11.

As a result of the aforementioned snap fit connection, the connecting assembly 50 will serve to retain the body 22 of the cap assembly 20 and in particular the flow restricting member 42 in enclosing relation with the tube or other nozzle portion 2' such that the interior 43 of the flow restricting portion 42 is in flow restricting relation to the elongated channel 30 and in particular the discharge port 4. Therefore, the interior 43 of the flow restricting member 42 is dimensioned and configured to snuggly receive and sealingly engage the nozzle tube 2' therein, such that the discharge port 4 is sealed against discharge of the contents of the preloaded syringe 11.

Once the tamper evident cap assembly 20 is operatively positioned on the nozzle 2, as represented in FIG. 2, a predetermined force sufficient to remove the body 22 from the syringe 11 and which is applied to the body 22, will be at least partially transferred to the flow restricting member 40 and to the one or more attachment members 48. Therefore, any force sufficient to accomplish removal of the body 22 will serve to fracture or break the interconnecting attachment members 48, thereby releasing or detaching the body 22 from its enclosing relation to the nozzle 2. However, due to the retaining engagement of the connecting assembly 50 with the interior, connecting portion 3" of the nozzle 2, the flow restricting member 42 will remain on the nozzle 2 in flow restricting relation to the discharge 4. As a result, the removal of the body 22 or its disconnection from the flow restricting member 42 will provide a clear indication that access to the interior of the preloaded syringe 11 has been attempted.

Authorized use of this syringe 11 and/or access to the contents thereof can be accomplished by exerting an additional, pulling force or other appropriately directed force on the flow restricting member 42, which will remain attached to the nozzle 2 of the syringe 11. Such application of the pulling or other force will cause the lips 54 of the flexible legs 52 of the connecting assembly 50 to be forced from their retaining, biased engagement with the connecting portion 3" of the nozzle 2 of the syringe 11.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A tamper evident cap assembly connectable to a syringe having a nozzle and a discharge port, said cap assembly comprising:
a body including a nozzle engaging portion disposed and structured to define a flow restricting member, said flow restricting member removably connected to said body on an interior thereof,
said flow restricting member disposed and structured to engage the nozzle in flow restricting relation to the discharge port,
an attachment assembly comprising at least one attachment member disposed within said interior of said body in interconnecting relation between an interior surface of said body and an exterior surface of said flow restricting member,
said attachment assembly structured to facilitate detachment of said flow restricting member from said body upon said body being removed from the syringe, wherein said attachment assembly comprises a plurality of attachment members disposed in spaced relation to one another about an outer periphery of said flow restricting member and in attached, interconnecting relation to said interior surface of said body and said exterior surface of said flow restricting member,
a connecting assembly mounted on said flow restricting member in retaining engagement with the nozzle, and
said attachment assembly and said connecting assembly cooperatively structured to maintain said retaining engagement of said flow restricting member with said nozzle, in flow restricting relation to the discharge port, upon detachment of flow restricting member from said body.

2. A cap assembly as recited in claim 1 wherein said attachment assembly is at least partially formed of a frangible material.

3. A cap assembly as recited in claim 1, wherein at least some of said attachment members are formed of a frangible material.

4. A cap assembly as recited in claim 1 wherein said attachment assembly is further structured to facilitate detachment of said flow restricting member from said body upon a predetermined force being exerted on said flow restricting member.

5. A cap assembly as recited in claim 1 wherein said attachment assembly is further structured to facilitate detachment of said flow restricting member from said body upon a predetermined force being exerted on said body.

6. A cap assembly as recited in claim 1 further comprising a connecting assembly mounted on said flow restricting member, said connecting assembly disposed and structured to define a snap-fit connection with the syringe.

7. A cap assembly as recited in claim 6 wherein said connecting assembly is cooperatively structured with the syringe to facilitate said snap-fit connection upon a substantially linearly directed force being exerted on said body in a direction toward the nozzle and concurrent to engagement between said flow restricting member and the nozzle.

8. A cap assembly as recited in claim 6 wherein said connecting assembly comprises a plurality of legs flexibly connected to said flow restricting member and disposable in biased engagement with a portion of the nozzle.

9. A cap assembly as recited in claim 8 wherein each of said plurality of legs comprises a free distal end and an outwardly projecting lip mounted on said free distal end, each of said lips disposable in a biased engagement with the nozzle to further define said snap-fit connection.

10. A cap assembly as recited in claim 9 wherein said snap-fit connection further comprises said plurality of lips disposed on an interior portion of said nozzle, said lips disposed in removable biased engagement with interior surface portions.

11. A tamper evident cap assembly connectable to a syringe having a nozzle and a discharge port, said cap assembly comprising:
a body connectable to the syringe in covering relation to the discharge port,
a flow restricting member removably connected to said body,
a connecting assembly mounted on said flow restricting member and disposable in retaining engagement with a portion of the nozzle,
said connecting assembly comprising a plurality of a least two legs each including a free distal end, said two legs flexibly connected to said flow restricting member, each of said free distal ends of each of said two legs including an outwardly projecting lip mounted thereon, each of said lips disposed in a biased, retaining engagement with interior surface portions of the nozzle to define a snap-fit connection there between, said flow restricting member disposed in flow restricting relation to the discharge port concurrent to said connecting assembly being disposed in said retaining engagement with the nozzle, an attachment assembly disposed within an interior of said body in attached, interconnecting relation between an interior surface of said body and an exterior surface of said flow restricting member, wherein said attachment assembly comprises a plurality of attachment members disposed in spaced relation to one another about an outer periphery of said flow restricting member, and said attachment assembly structured to facilitate detachment of said flow restricting member from said interior of said body upon said body being removed from the syringe.

12. A cap assembly as recited in claim 11 wherein said attachment assembly is further structured to facilitate detachment of said flow restricting member from said body upon a predetermined force being exerted on said body.

13. A cap assembly as recited in claim 12 wherein said attachment assembly is at least partially formed of a frangible material.

14. A cap assembly as recited in claim 11 wherein said connecting assembly is cooperatively structured with the syringe to facilitate said snap-fit connection upon a substantially linearly directed force being exerted on said body in a direction toward and substantially coaxial with the nozzle.

15. A cap assembly as recited in claim 11 wherein said flow restricting member is disposed in enclosing relation to the discharge port when said legs are in said retaining engagement with the nozzle.

16. A cap assembly as recited in claim 11 wherein said flow restricting member comprises an open, hollow interior portion dimensioned and configured to receive the discharge port therein, said flow restricting member disposed in enclosing relation to the discharge port when said connecting assembly is disposed in said retaining engagement with the nozzle.

17. A cap assembly as recited in claim 11 wherein said attachment assembly and said connecting assembly are cooperatively structured to maintain said retaining engagement of said flow restricting member with the nozzle, in flow restricting relation to the discharge port, upon the detachment of said flow restricting member from said body.

* * * * *